(12) United States Patent
Sussner et al.

(10) Patent No.: US 10,436,737 B2
(45) Date of Patent: Oct. 8, 2019

(54) GAS SENSOR WITH HUMIDITY CORRECTION

(71) Applicant: MATRIX SENSORS, INC., San Diego, CA (US)

(72) Inventors: Heinrich Sussner, Palo Alto, CA (US); Paul R Wilkinson, El Segundo, CA (US); Steven Yamamoto, San Diego, CA (US); David K Britt, El Cerrito, CA (US)

(73) Assignee: MATRIX SENSORS, INC., San Diego, CA (US)

( * ) Notice: Subject to any disclaimer, the term of this patent is extended or adjusted under 35 U.S.C. 154(b) by 0 days.

(21) Appl. No.: 15/872,999

(22) Filed: Jan. 17, 2018

(65) Prior Publication Data

US 2018/0202961 A1     Jul. 19, 2018

Related U.S. Application Data

(60) Provisional application No. 62/447,429, filed on Jan. 17, 2017.

(51) Int. Cl.
*A61B 5/055*     (2006.01)
*G01N 27/327*     (2006.01)
(Continued)

(52) U.S. Cl.
CPC ......... *G01N 27/3271* (2013.01); *A61B 5/055* (2013.01); *G01N 27/026* (2013.01);
(Continued)

(58) Field of Classification Search
CPC .. G01N 27/3271; G01N 27/026; A61B 5/055; A61B 2562/028; B81B 2201/06
See application file for complete search history.

(56) References Cited

U.S. PATENT DOCUMENTS

| 4,760,351 | A | * | 7/1988 | Newell | ..................... G04F 5/06 310/320 |
| 5,668,303 | A | | 9/1997 | Giesler | |
| 6,223,588 | B1 | * | 5/2001 | Burgass | ............... G01N 25/085 73/19.01 |
| 6,360,585 | B1 | | 3/2002 | Potyrailo | |

(Continued)

*Primary Examiner* — John E Breene
*Assistant Examiner* — Eyob Hagos
(74) *Attorney, Agent, or Firm* — Mark B. Floyd (57) ABSTRACT

A device and method are provided for detecting analyte with correction for the effects of humidity. The device comprises a resonant sensor having an oscillating portion. A capacitor is positioned on the oscillating portion. The capacitor is formed by at least two electrodes and a sensing material positioned between the electrodes. A readout circuit is arranged to measure a response of the oscillating portion (e.g., frequency shift or change in resonance frequency, stiffness or strain) and a capacitance of the capacitor when substances are adsorbed or absorbed in the sensing material. This combination of measurements enables the device to distinguish between various types of adsorbed or absorbed molecules, especially distinguishing between an analyte of interest and water molecules that might interfere with the detection of the analyte. A processor determines an analyte value indicative of the presence, amount or concentration of the analyte in dependence upon measurements of both the response of the oscillating portion and the capacitance to account for the effects of water in the sensing material.

20 Claims, 8 Drawing Sheets

(51) Int. Cl.
  *G01N 27/02*   (2006.01)
  *G01N 29/00*   (2006.01)
  *G01N 29/02*   (2006.01)
  *G01N 29/036*  (2006.01)
  *G01N 29/24*   (2006.01)
  *G01N 29/44*   (2006.01)
  *A61B 5/00*    (2006.01)
  *A61B 5/145*   (2006.01)

(52) U.S. Cl.
  CPC .......... *G01N 29/00* (2013.01); *G01N 29/022* (2013.01); *G01N 29/036* (2013.01); *G01N 29/2406* (2013.01); *G01N 29/4427* (2013.01); *A61B 5/14503* (2013.01); *A61B 5/14546* (2013.01); *A61B 5/686* (2013.01); *A61B 2562/028* (2013.01); *A61B 2562/029* (2013.01); *B81B 2201/06* (2013.01); *G01N 2291/0256* (2013.01); *G01N 2291/02809* (2013.01); *G01N 2291/02845* (2013.01); *G01N 2291/0426* (2013.01); *G01N 2291/0427* (2013.01)

(56) References Cited

U.S. PATENT DOCUMENTS

| | | |
|---|---|---|
| 7,305,883 B2 | 12/2007 | Khuri-Yakub |
| 7,568,377 B2 | 8/2009 | Bhethanabotla |
| 7,667,369 B2 | 2/2010 | Haskell |
| 7,812,622 B1 | 10/2010 | Sun |
| 7,955,560 B2 | 6/2011 | Centanni |
| 8,065,904 B1 | 11/2011 | Allendorf |
| 8,480,955 B2 | 7/2013 | Yaghi |
| 8,718,956 B2 | 5/2014 | Hesketh |
| 8,733,154 B2 | 5/2014 | Cable |
| 8,735,161 B2 | 5/2014 | Yaghi |
| 8,776,597 B2 | 7/2014 | Waga |
| 8,793,849 B1 | 8/2014 | Bhethanabotla |
| 9,239,308 B2 | 1/2016 | Tondokoro |
| 2007/0138909 A1* | 6/2007 | Mortet ................. G01N 29/022 310/318 |
| 2010/0180673 A1* | 7/2010 | Cable ................... G01N 29/036 73/64.53 |
| 2012/0071362 A1* | 3/2012 | Nhan ................... G01N 33/0047 506/33 |
| 2015/0064723 A1 | 3/2015 | Mutharasan |
| 2015/0177196 A1* | 6/2015 | Sussner ............... G01N 29/2406 73/24.04 |
| 2016/0187280 A1 | 6/2016 | Potyrailo |
| 2016/0202225 A1 | 7/2016 | Feng |

* cited by examiner

GAS SENSOR WITH HUMIDITY CORRECTION

CROSS REFERENCE TO RELATED APPLICATIONS

This application claims the benefit of U.S. provisional patent application 62/447,429 filed on Jan. 17, 2017 which application is hereby incorporated by reference in its entirety.

BACKGROUND

The invention relates generally to sensors for detecting substances, and in particular to sensors for detecting gases in the presence of humidity.

Chemical sensing of gases is an important technology in several fields including environmental monitoring, industrial safety, and public security. Depending on the application and target gas, different operating principles have been deployed, ranging from electrochemical, metal-oxide semiconductor, and non-dispersive infrared absorption. With the recent advancement of smartphones, wearables, and connected sensor devices, many more chemical sensing applications have emerged. In particular monitoring the health, safety and well being of consumers is receiving considerable interest. The problem is that existing technologies listed above do not meet the needs of these emerging applications. Specifically, existing devices lack specificity and have a relatively large size, power requirement and cost.

One problem to overcome is that resonant chemical sensors can be highly sensitive to even moderate changes in relative humidity. When measuring an analyte in ambient environmental conditions, the sensor indicates not only a mass change due to the target gas, but also due to the additional adsorption of water molecules in the sensing material. While many sensing materials can be tailored to detect specific analyte molecules with low cross sensitivity, the absorption of water molecules is a more difficult problem to solve due its omnipresence and chemical activity.

There have been multiple approaches documented in the literature to address the problem of water interference for chemical sensing. These approaches include the design of a hydrophobic receptor material, the incorporation of filters and membranes to block water access, the addition of a second sensor with different water affinities (as described in US 20130311108 A1), or adding a separate humidity sensor as a reference (as described in U.S. Pat. No. 7,887,683 B2). Each of these methods has serious limitations. For example, a hydrophobic receptor material—if it can be found—often has reduced sensitivity for the analyte due to the trade off in the material characteristics. The addition of a filter or membrane increases cost and raises the issue of saturation, desorption and hysteresis of the filter which can affect the measurement and longevity of the device. Adding a separate relative humidity sensor fails because commercially available humidity sensors lack the required precision and accuracy. Adding a second sensing material to monitor water adsorption is problematic because the two sensing materials are not exactly identical and the differences between them causes errors too large to overcome, especially over time. Finally, most of these approaches increase cost, size and complexity. There is still a need for a simple, low cost, miniaturized sensor to detect analyte that accounts for the effects of humidity and water adsorption by the sensing material.

SUMMARY

According to an aspect, a sensor device is provided for detecting at least one analyte with correction for the effects of humidity. The device comprises at least one resonant sensor having an oscillating portion. At least one capacitor is positioned on the oscillating portion. The capacitor is formed by at least two electrodes and a sensing material positioned between the electrodes. At least one readout circuit is arranged to measure both a response of the oscillating portion (e.g., a frequency shift or a change in resonance frequency, dissipation, quality factor, stiffness, or strain) and a capacitance of the capacitor when substances are adsorbed or absorbed in the sensing material. This combination of measurements enables the device to distinguish between various types of adsorbed or absorbed molecules, especially distinguishing between an analyte of interest (e.g., carbon dioxide or methane) and water molecules that might interfere with the detection of the analyte. In some embodiments, a processor is programmed to determine an analyte value indicative of the presence, amount or concentration of the analyte in dependence upon measurements of both the response of the oscillating portion and the capacitance to account for the effects of water in the sensing material.

According to another aspect, a sensor device is provided for detecting at least one analyte with correction for the effects of humidity. The device comprises at least one resonator having an oscillating portion. First and second electrodes are coupled to first and second sides of the resonator. The first and second electrodes are positioned to apply a potential difference across the resonator to drive an oscillating motion of the oscillating portion. A sensing material is disposed on the second electrode. The sensing material adsorbs or absorbs the analyte, if present. A third electrode is disposed on the sensing material such that the sensing material is positioned between the second and third electrodes. The third electrode is gas-permeable. At least one readout circuit is arranged to measure a response of the oscillating portion and a capacitance of the capacitor formed by the second and third electrodes when substances are adsorbed or absorbed in the sensing material. In some embodiments, a processor is programmed to determine an analyte value indicative of the presence, amount or concentration of the analyte in dependence upon measurements of both the response of the oscillating portion and the capacitance to account for the effects of water in the sensing material.

According to another aspect, a method is provided for detecting at least one analyte with correction for the effects of humidity. At least one resonant sensor is exposed to a sample or to an environment potentially containing the analyte and water vapor. The resonant sensor includes at least one oscillating portion and at least one capacitor positioned on the oscillating portion. The capacitor is formed by at least two electrodes and a sensing material positioned between the electrodes. The method comprises the steps of measuring a response of the oscillating portion and a capacitance of the capacitor when substances are adsorbed or absorbed in the sensing material. At least one processor is utilized to determine at least one analyte value indicative of the presence, amount or concentration of the analyte according to the measurements of both the response of the oscillating portion and the capacitance to account for the effects of water in the sensing material.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. Unless otherwise required, any described method steps need not be necessarily performed in a particular illustrated order. Making a determination or decision in dependence upon (or according to) a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links. According to some embodiments, the present invention provides, inter alia, computer systems comprising hardware (e.g. one or more processors and associated memory) programmed to perform the methods described herein, as well as computer-readable media encoding instructions to perform the methods described herein.

Resonant sensors use a sensing material to adsorb or absorb target molecules that change properties that are reflected in a mechanical or electromechanical response of the sensor, such as a frequency shift or a change in resonance frequency, dissipation, quality factor, stiffness, or strain. The response of the resonant sensor is often detected using an electrical property, such as a change in impedance of the circuit driving an oscillating motion of the sensor. Many electrical detection methods and optical detection methods are known in the art to detect a frequency shift or a change in resonance frequency, dissipation, quality factor, stiffness, or strain of a resonant sensor or array of resonant sensors.

A wide variety of cantilever, membrane and piezoelectric resonator-based sensors have been fabricated using Micro-Electro-Mechanical Systems (MEMS) technology. These sensors generally detect substances through the use of sensing material (e.g., a polymer film or a metal-organic framework) with selective adsorption for a specific analyte (e.g., molecules of the gas of interest). Resonant sensors are sensitive to small amounts of water vapor even at moderate levels of relative humidity. When measuring an analyte in ambient conditions, the sensor may indicate a mass change not only due to the target gas, but also due to the additional adsorption of water molecules in the sensing material.

Figure 1:
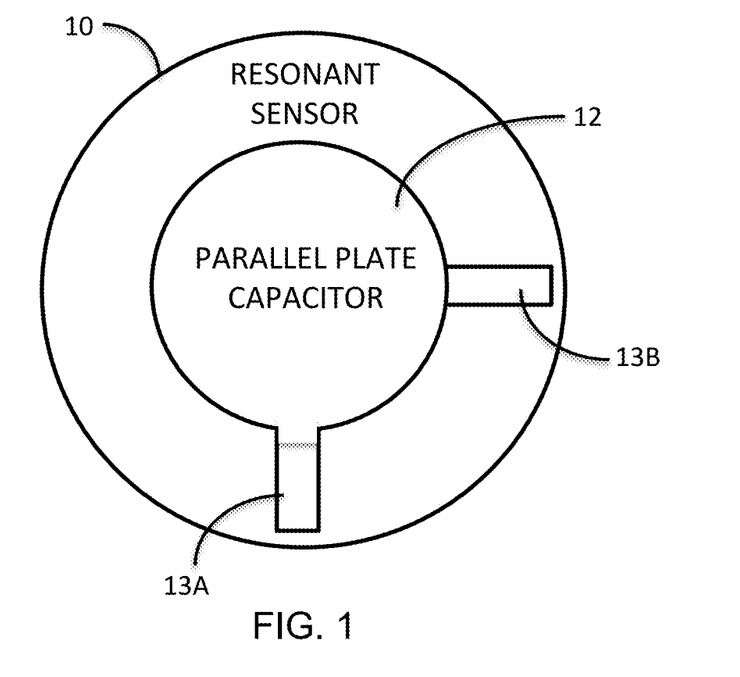
FIG. 1 is a top plan view of a resonant sensor and a parallel plate capacitor according to a first embodiment of the invention.

FIG. 1 shows a resonant sensor 10 and a parallel-plate capacitor 12 that is positioned on the oscillating portion of the resonant sensor 10. The resonant sensor 10 is preferably a quartz crystal microbalance (QCM). There are many other mechanical resonators suitable for use including but not limited to cantilevers, capacitive micromachined ultrasonic transducers (cMUTs), Piezoelectric Micromachined Ultrasonic Transducers (PMUT), thin-film bulk acoustic resonator (FBAR or TFBAR), or other MEMs transducers. The quartz crystal typically has a circular surface, and the parallel-plate capacitor 12 is positioned on the oscillating portion of the QCM substantially at the center of the circular surface. The capacitor is formed by two electrodes having respective electrical contact pads 13A, 13B.

The capacitor 12 provides a capacitance measurement that is useful to determine the amount of water vapor that is adsorbed or absorbed in the sensing material on the resonant sensor 10. The capacitance measurement is combined with the measurement of the mechanical or electromechanical response of the resonant sensor 10, such as a frequency shift or a change in resonance frequency, dissipation, quality factor, stiffness, or strain. This combination of electromechanical and capacitance measurements enables the device to distinguish between various types of adsorbed or absorbed molecules, especially distinguishing between an analyte of interest (e.g., carbon dioxide or methane) and water molecules that might interfere with the detection of the analyte. The capacitance measurement is useful to determine how much of the response of the resonator is due to water, and thus how much of the response of the resonator is due to a mass of analyte in the sensing material.

Figure 2:
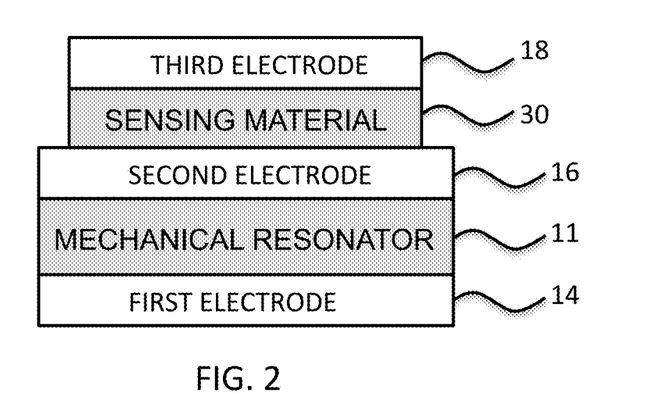
FIG. 2 is a schematic, side view of a mechanical resonator and a capacitor sharing a common electrode.

FIG. 2 shows a side view of a resonant sensor that includes a mechanical resonator 11 (e.g., a quartz crystal), a first (back) electrode 14 coupled to a back side of the resonator 11, and a second (front) electrode 16 that is coupled to a front side of the resonator 11. The first and second electrodes 14 and 16 are positioned to apply a potential difference across the resonator 11 to drive an oscillating motion of the resonator 11. The first and second electrodes 14 and 16 are typically gold. A sensing material 30 is disposed on the second electrode 16. The sensing material 30 at least partially covers the second (front) electrode 16. In some embodiments, the sensing material 30 covers the electrode 16 completely, although complete coverage is not necessary. The layer of the sensing material 30 on the second electrode 16 should be sufficient to adsorb enough analyte (if present in the environment or sample to which the resonant sensor is exposed) to change the oscillation of the resonant sensor due to the mass of the analyte adsorbed. The sensing material 30 is preferably an adsorbing film (e.g., a metal-organic framework or a polymer film) that is grown or deposited directly on the front electrode 16.

The parallel-plate capacitor is formed by the second electrode 16 and a third electrode 18 disposed on the sensing material 30. If the resonator 11 is a QCM, the first electrode 14 is the back electrode, and the second electrode 16 is the front electrode. The second (front) electrode 16 is preferably grounded, and the capacitor shares the grounded second electrode 16 with the resonator 11 in this embodiment. The third electrode 18 is preferably deposited or grown on top of the sensing material 30. The third electrode 18 should be gas-permeable (e.g. porous, slotted, interdigitated, or serpentine) to ensure that the sensing material 30 is accessible to analyte molecules in a sample or in the environment to which the sensor is exposed.

The sensing material 30 is preferably a porous crystalline material such as a metal-organic framework (MOF), porous coordination polymer, or porous coordination framework. Preferred MOF subclasses include Zeolitic imidazolate framework (ZIF), IRMOF, and Multivariate MOF (MTV-MOF) made using a mix of organic linkers having the same geometry but varied chemical functionality. Suitable porous sensing materials also include a covalent organic framework (COF) in which the framework includes covalent chemical bonds rather than metal coordination bonds, and Zeolite which is a class of inorganic porous crystalline materials. In rare embodiments, the porous sensing materials comprise non-crystalline porous materials such as Metal-organic Polyhedron having discreet porous cages, Porous metal-organic polymer, Metal-organic gel, or Porous Carbon (also known as activated carbon).

Metal-organic frameworks (MOFs) are an expanding class of porous crystalline materials that are built up from nodes of metal ions connected by organic linkers. These materials can typically be engineered to have pore apertures with a width or diameter in a range of less than 1 Angstrom to about 30 Angstroms (Yaghi, et. al., Nature 423, 705-714, Jun. 12, 2003). A class of exotic MOFs ("MOF-74") with pore aperture diameters of 98 Angstroms have also been demonstrated (Deng, et. al., Science 336, 1018, 2012). MOFs with varying pore sizes can selectively adsorb molecules based on the size of the molecules. For example, engineered MOFs with pore sizes designed for carbon dioxide ($CO_2$) adsorption can separate gases in industrial processes (Du, et. al., J. Am. Chem. Soc., 2013, 135 (2), pp 562-565). MOFs can also be used as sensing material with a QCM to act as a chemical sensor in controlled environments. When one or more types of MOFs is used as a sensing material on a resonant sensor, the surface on which the MOF is grown may be prepared for MOF growth with a self-assembled monolayer (SAM) or by deposition of either an oxide or metal surface. The MOF coating on the oscillating portion of the sensor typically has a thickness in the range of 1 to 1000 nm. MOFs can be designed with different pore sizes and specific chemical affinities to target specific gases with high selectivity.

In other embodiments, the sensing material 30 is a polymer film. Polymer sensing materials respond to gas-phase analytes in a time frame of seconds to tens of minutes. The selection of the polymer sensing material is preferably optimized to fit the mechanical properties of the resonator (elasticity, density, thickness, etc.), so that detection time is minimized and sensitivity is maximized. Sensors may be coated or functionalized with various types of sensing materials for specific applications. These possible sensing materials include, for example, porous receptor materials as listed above, polymers (co-polymers, bio-polymers), sol gels, and DNA, RNA, proteins, cells, bacteria, carbon nanotube arrays, catalysts including metals to enzymes, nanoclusters, organic and inorganic materials including: supramolecules, metal-organic complexes, or dendritic materials.

The second and third electrodes 16 and 18 preferably comprise substantially parallel layers or plates of metal, and a layer of the sensing material 30 is positioned between the parallel layers or plates of metal. The electrodes typically include respective electrical contact pads 13A, 13B (shown in FIG. 1 but not shown in FIG. 2), and the third electrode 18 is gas-permeable (e.g., there are holes or openings in the electrode to permit molecules to pass through to the sensing material 30). Thus, it is not necessary for the entire portion of each electrode to be a parallel plate that is fully intact, since the contact pad, holes, or other parts of each electrode may not exactly resemble a parallel plate. Instead, it is preferred that each of the electrodes 16 and 18 has a major portion that is at least one layer of metal (that may include holes to be gas-permeable) that lies in a plane substantially parallel to the plane of the other electrode. Each electrode may include some other parts (e.g., electrical contact pads) that are not necessarily part of the parallel layer of metal. The contact pads preferably extend outwardly from the major portions of the electrodes to the edges or the non-oscillating portion of the quartz crystal. At that point, the contact pads connect to the holder of the quartz and in turn into vias or larger pads, as is known in the art. It is understood that the invention covers other variations of capacitor designs which may include guard rings, etc.

The capacitor formed by the second and third electrodes 16, 18 should be positioned on the oscillating portion of the resonator 11. The term "oscillating portion" is intended to mean the portion, region, or member of the resonator that oscillates. For example, the oscillating portion for a QCM typically comprises the piezoelectric material vibrating between the first and second electrodes 14 and 16. For a cantilever type of resonant sensor, the oscillating portion is the cantilever beam and the capacitor is positioned on the beam. For a cMUT type of resonant sensor, the oscillating portion is typically a vibrating membrane and the capacitor is positioned on the membrane. With an FBAR type of resonant sensor, the oscillating portion typically comprises the piezoelectric material and the electrodes positioned to apply a potential difference across the piezoelectric material, etc.

The positioning of the capacitor on the oscillating portion of the resonator 11 enables the device to measure the mechanical or electromechanical response to the mass of substances (e.g., analyte of interest and water) that are adsorbed or absorbed in the sensing material 30 and to measure the capacitance change due to the adsorption or absorption of substances in exactly the same sensing material 30 at the same temperature and point in time. The capacitance measurement indicates how much of the response of the resonator 11 (e.g., frequency shift or change in resonance frequency, stiffness or strain) is due to water in the sensing material 30, and thus how much of the response of the resonator 11 is due to an amount of the target analyte adsorbed or absorbed in the sensing material 30. Water has a much higher relative permittivity than the analyte of interest, so that the presence of water in the sensing material 30 greatly changes the capacitance measurement, while the presence of molecules of the target gas often has a negligible effect on the capacitance measurement due to the much lower relative permittivity of the analyte. The capacitance, C, of a parallel plate capacitor is given by equation (1):

$$C = \kappa \epsilon_0 A/t \quad (1)$$

where κ is the relative permittivity, $\epsilon_o$ is the permittivity of free space, A is the capacitor electrode area, and t is its thickness. As molecules of high relative permittivity adsorb or absorb to the sensing material 30, the capacitance increases. Table 1 shows the relative permittivity and mass of a few common solvents, including water, which is the interferent of greatest interest.

TABLE 1

| Solvent | κ | m |
|---|---|---|
| Benzene | 2.27 | 78.11 |
| methanol | 24.5 | 32.04 |
| ethanol | 32.7 | 46.1 |
| Isopropanol | 17.9 | 60.1 |
| Cyclohexane | 2.02 | 84.1 |
| Methane | 1.04 | 16 |
| Carbon Dioxide | 1.63 | 44 |
| water | 80.1 | 18 |

Water has a much higher relative permittivity than the potential analyte(s) of interest, such as methane and carbon dioxide. The adsorption of analytes is detected by monitoring the frequency of a mechanical resonator that is coated with the sensing material 30. Adsorption of an analyte in the sensing material 30 increases the mass and lowers the frequency of the resonator and vice versa when the gas is desorbed according to the equation:

$$\frac{\Delta f}{f_o} = -\frac{1}{2}\frac{\Delta m}{m_o} \quad (2)$$

where $f_o$ is the resonant frequency and $m_o$ is the mass of the resonator before mass loading. Noting that the change in mass is due to accumulation of N molecules of weight, $m_{mol}$, we have equation 3:

$$\Delta f = -\frac{f_o}{2m_o} m_{mol} N \quad (3)$$

The problem is to determine how much of the mass loading and resulting frequency shift is due to humidity (water molecules) in the sensing material 30, and how much is due to molecules of the target analyte, if any. To solve the humidity problem, two measurements are made on the same sensing material 30. First, the capacitance of the capacitor formed by the second and third electrodes 16 and 18 is measured to determine the amount of water in the sensing material 30. Second, the mechanical or electromechanical response (e.g., frequency shift) of the resonator 11 to mass loading is measured to determine the total combined mass of the gas absorption (analyte and water vapor) in the sensing material 30. The measurements of the oscillator response (e.g., frequency) and the capacitance may be taken at the same time or sequentially, and the order of measurements may be reversed.

Water usually has a much higher dielectric constant than the analyte(s) of interest, so the capacitance measurement signal corresponds to the amount of water in the sensing material 30 independent of the amount of analyte in the sensing material. Many gas analytes, such as methane and carbon dioxide, do not affect the capacitance, or their effect on the capacitance is negligible. The total combined mass adsorbed in the sensing material 30 corresponds to the sum of the mass of analyte plus the mass of water in the sensing material. The capacitance measurement is used to calculate the contribution of water to the change in frequency (or whatever detection signal is chosen to measure the response of the oscillator if not frequency), and thus the contribution of water to the total combined mass adsorbed in the sensing material 30. The change in frequency of the resonator 11 indicates the combined mass adsorbed, and the contribution of water is subtracted (or accounted for using algorithms, calibration curves or data, and/or look-up tables) from the combined mass of the analyte plus water vapor adsorbed in the sensing material 30 to determine the amount of the analyte present, if any. In this way, the device is able to determine an accurate analyte value (e.g., mass or concentration) independent of humidity fluctuations.

Figure 3:
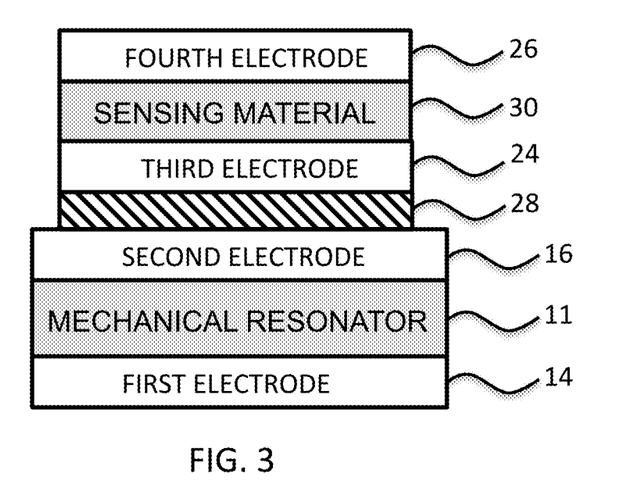
FIG. 3 is a schematic, side view of a capacitor disposed on an oscillating portion of a resonant sensor according to another embodiment of the invention.

FIG. 3 shows another embodiment of a resonant sensor having an oscillating portion and a capacitor positioned on the oscillating portion to measure the change in capacitance when water molecules are adsorbed in the sensing material 30. In this example, the device includes four electrodes rather than three electrodes as previously described. As in the previous example, the resonant sensor includes the mechanical resonator 11 and first and second electrodes 14 and 16 coupled to opposite sides of the resonator 11. The first and second electrodes 14 and 16 are positioned to apply a potential difference across the resonator to drive an oscillating motion of the oscillating portion of the resonator 11.

The capacitor is formed by third and fourth electrodes 24 and 26 with the sensing material 30 positioned between the third and fourth electrodes 24 and 26. In this example, the capacitor is preferably positioned on the oscillating portion of the resonator 11 by means of at least one insulating layer 28 that separates the third electrode 24 from the second electrode 16. Examples of suitable materials for the insulating layer include $SiO_2$, SiN, $Al_2O_3$ or AlN. The third and fourth electrodes 24 and 26 preferably comprise substantially parallel layers or plates of metal to form essentially a parallel plate type of capacitor. The fourth electrode 26 should be gas-permeable (e.g. porous, slotted, interdigitated, or serpentine) to ensure that the sensing material 30 is accessible to molecules in a sample or environment to which the sensor is exposed.

Figure 4A:
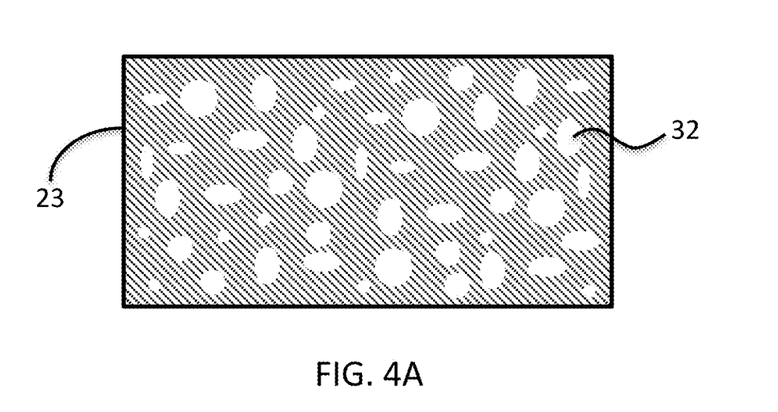
FIGS. 4A-E are schematic plan views of five different types of gas-permeable electrodes for a capacitor according to some embodiments of the invention.
Figure 4B:
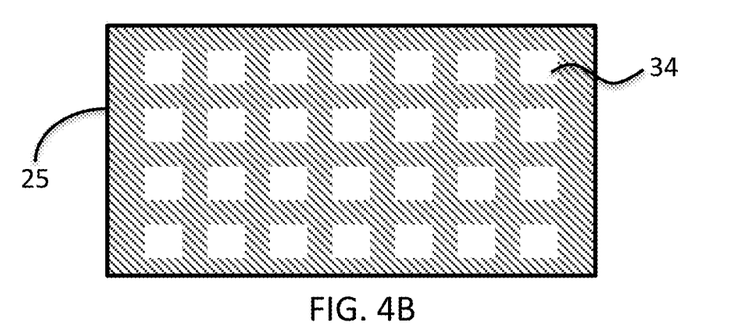
Figure 4C:
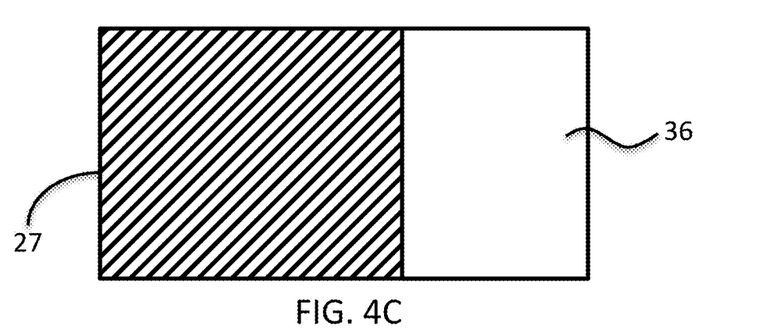
Figure 4D:
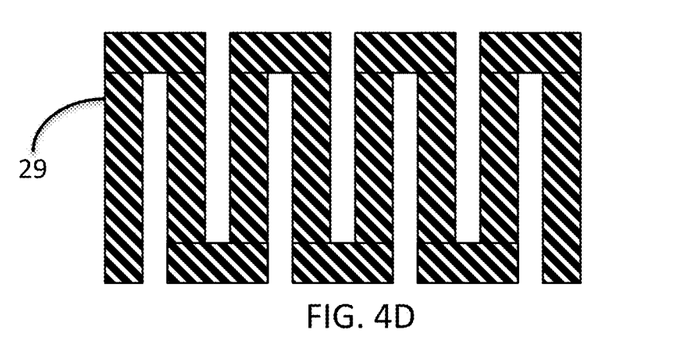
Figure 4E:
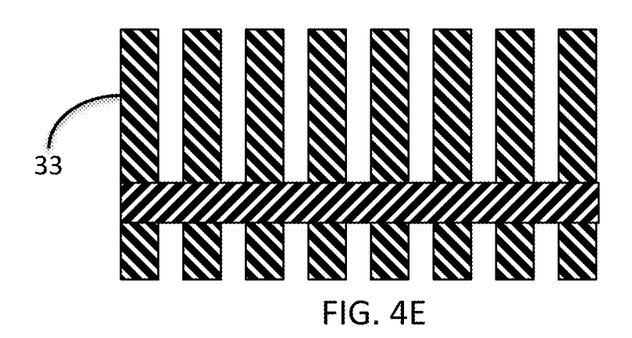

FIGS. 4A-E show different examples of designs for a gas-permeable electrode suitable for use as the outer electrode in the capacitor, to permit molecules of analyte to reach the sensing material. For example, the gas-permeable electrode may be porous platinum. FIG. 4A shows another electrode 23 having vias or holes 32 of varying shapes and sizes that may be formed in a masking process with polystyrene spheres. FIG. 4B shows an electrode 25 having holes 34 of substantially uniform shapes and spacing. The holes 34 can be formed using a photolithographic process. FIG. 4C shows an electrode 27 having an exposed opening 36 that may be formed to provide fractional coverage with a shadow mask. FIG. 4D shows a gas-permeable electrode 29 having no holes, but it does have a serpentine pattern or shape that may be lithographically defined. FIG. 4E shows another gas-permeable electrode 33 having a comb pattern or shape that may be lithographically defined. The vertical strips of the electrode 33 are connected by a continuous horizontal strip at the top, bottom, or along some portion therebetween.

There are several methods for producing a porous metal film suitable for use as a gas-permeable electrode. A first technique is by direct deposition of a porous metal film (e.g. oblique angle sputtering). A second technique is post processing of a metal film (e.g. co-sputtering of two metals followed by selective de-alloying). A third technique is masked deposition of a metal film using the following types of masks: (a) photolithographic process (using photoresist) to define openings as ordered or random slits or holes (e.g. the snaking, comb, and mesh embodiments); (b) use of a stencil mask; or (c) use of particles as a mask that is either removed or left behind (e.g. polystyrene spheres).

Figure 5A:
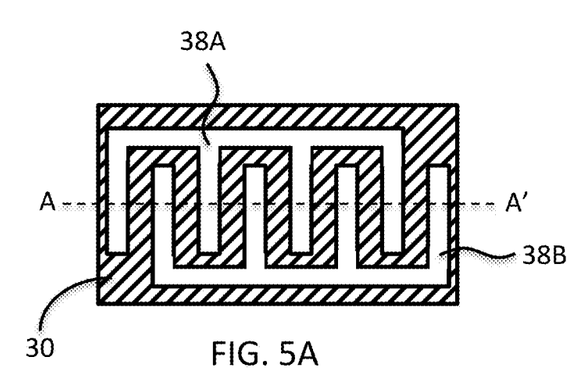
FIG. 5A is a top plan view of a sensor element having an interdigitated capacitor positioned on a resonator according to another embodiment of the invention.
Figure 5B:
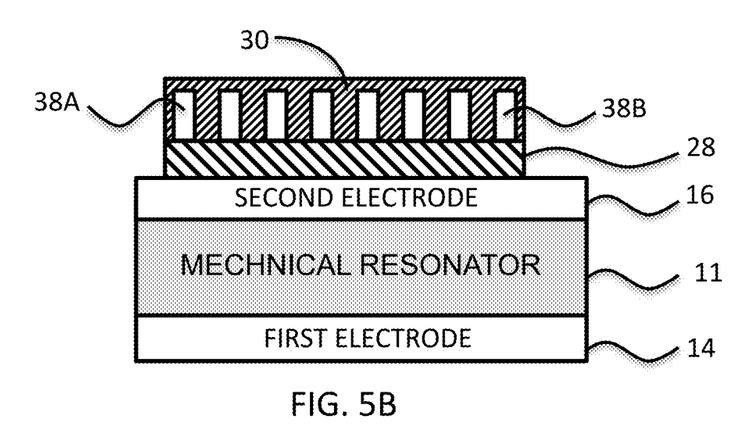
FIG. 5B is a cross-sectional view of the sensor element of FIG. 5A along the line A-A'.

FIG. 5A shows a top view of another embodiment with interdigitated electrodes 38A, 38B forming the capacitor. The sensing material 30 is positioned between the interdigitated electrodes 38A, 38B. FIG. 5B is a cross-sectional view of the sensor element of FIG. 5A along the line A-A'. In this example, the device includes four electrodes. The resonant sensor includes the mechanical resonator 11 and first and second electrodes 14, 16 coupled to opposite sides of the resonator 11, as in previous examples. The first and second electrodes 14, 16 are positioned to apply a potential difference across the resonator 11 to drive an oscillating motion of the resonator. The capacitor is formed by third and fourth electrodes 38A and 38B. The third and fourth electrodes 38A and 38B are interdigitated so that the sensing material 30 is accessible to both analyte and water molecules in a sample or environment to which the sensor is exposed. The interdigitated capacitor is positioned on the oscillating portion of the resonator 11 by means of the insulating layer 28 (e.g., $SiO_2$, SiN, $Al_2O_3$ or AlN) that separates the third and fourth electrodes 38A and 38B from the second electrode 16.

Figure 6:
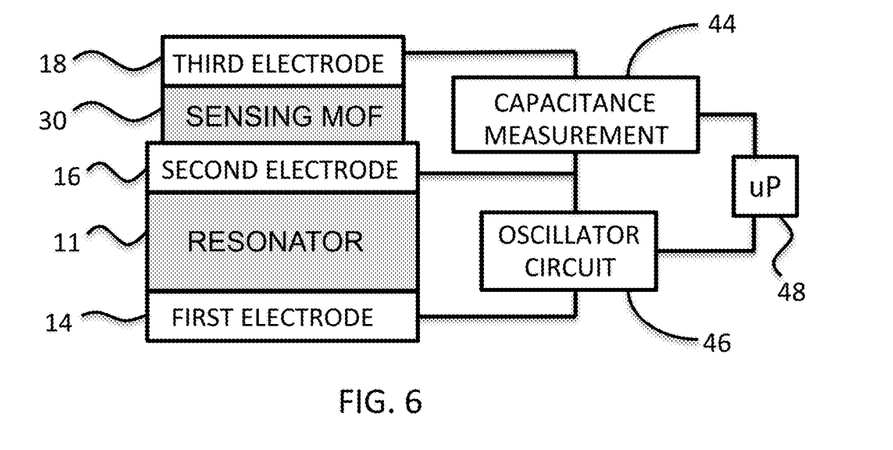
FIG. 6 is a schematic block diagram of a readout circuit connected to a sensor element having three electrodes, according to some embodiments of the invention.

FIG. 6 is a schematic block diagram of an electronic readout circuit connected to a resonant sensor with a capacitor. In this example, the sensor device has three electrodes (as described above with reference to FIG. 2). There are many suitable ways to configure one or more readout circuits to measure both a response of the oscillating portion and a capacitance of the capacitor when substances are adsorbed or absorbed in the sensing material 30. Thus, the term "at least one readout circuit" includes embodiments in which both measurements are accomplished with a single electronic readout circuit, or other embodiments where separate electromechanical and capacitance measurements are accomplished by a plurality of separate readout circuits.

In this example, an oscillator circuit 46 is connected to the first electrode 14 and to the second electrode 16 to drive the oscillating motion of the resonator 11 and to measure a mechanical or electromechanical response of the oscillating portion when substances are adsorbed or absorbed in the sensing material 30. The sensing material is preferably a MOF film. Suitable oscillator circuits for the readout include the Colpitts, Pierce, or Butler oscillator circuits. A capacitance measurement circuit 44 is connected to the second electrode 16 (shared electrode) and to the third electrode 18 to measure a capacitance of the capacitor formed by the second and third electrodes 16 and 18 when the substances are adsorbed or absorbed in the sensing material 30. The measurement of capacitance can be accomplished via a high-precision capacitance measurement method, such as but not limited to a relaxation oscillator or a Σ-Δ capacitance-to-digital converter. At least one processor 48 is in communication (wirelessly or with wires) with the oscillator circuit 46 and the capacitance measurement circuit 44 to receive signals or data indicative of the electromechanical response and the capacitance.

Figure 7:
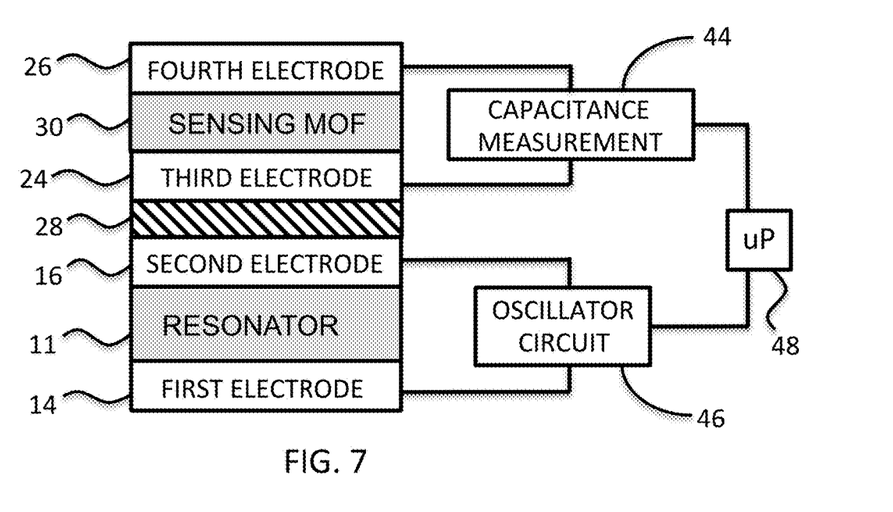
FIG. 7 is a schematic block diagram of a readout circuit connected to a sensor element having four electrodes, according to another embodiment of the invention.

FIG. 7 is a schematic block diagram of a similar electronic readout circuit connected to a sensor element having four electrodes, rather than 3 electrodes. The oscillator circuit 46 is connected to the first electrode 14 and the second electrode 16 to drive the oscillating motion of the resonator 11 and to measure a mechanical or electromechanical response of the oscillating portion when substances are adsorbed or absorbed in the sensing material 30, preferably a MOF film. The capacitance measurement circuit 44 is connected to the third electrode 24 and the fourth electrode 26 to measure a capacitance of the capacitor formed by the third and fourth electrodes 24 and 26 when the substances are adsorbed or absorbed in the sensing material 30. The processor 48 is in communication with the oscillator circuit 46 and the capacitance measurement circuit 44 to receive signals or data indicative of the electromechanical response and the capacitance. Although the oscillator circuit 46 and capacitance measurement circuit 44 are drawn separately for simplicity of understanding in the patent drawings, they are typically part of the same overall electronic readout circuit under the control of the microprocessor 48.

Figure 8:
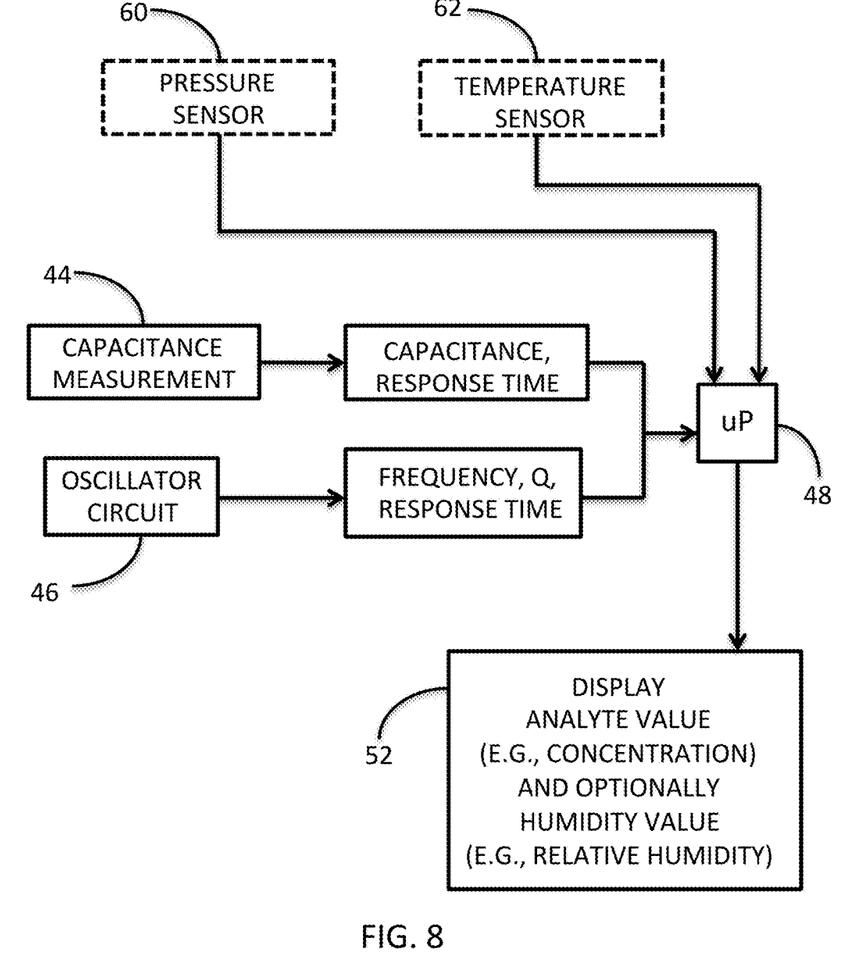
FIG. 8 is a schematic block diagram of readout circuits communicating with a processor that outputs calculated analyte and humidity values, according to some embodiments of the invention.

FIG. 8 is a schematic block diagram of the oscillator circuit 46 and the capacitance measurement circuit 44 communicating with the processor 48 that outputs a calculated analyte value and optionally a humidity value (e.g., a relative humidity value). The processor 48 is programmed to determine at least one analyte value indicative of the presence, amount or concentration of the analyte in dependence upon measurements of both the response of the oscillator 11 and the capacitance to account for the effects of water in the sensing material. In some embodiments, the analyte value may be a binary value such as "PRESENT" or "ABSENT" for the analyte, or present above a desired limit or threshold. More preferably, the analyte value is a number such as a concentration, amount or mass of the analyte. The analyte and/or humidity values may optionally be displayed to an end-user via the display 52 in communication with the processor 48. In some embodiments, an optional pressure sensor 60 and an optional temperature sensor 62 (e.g., thermistor) may be connected to the microprocessor 48. The microprocessor 48 is programmed to determine capacitance vs. relative humidity (RH) at various temperatures (and optionally pressures).

There are many possible methods or algorithms in which measurements of both capacitance and response of the oscillating portion may be used to calculate the analyte value and optionally a humidity value. In general, the capacitance measurement indicates the amount of water in the sensing material or it indicates how much of the response of the resonator (e.g., frequency shift or resonance frequency, stiffness or strain) is due to water in the sensing material, and thus the processor 48 can calculate how much of the response of the resonator is due to a mass of the target analyte adsorbed or absorbed in the sensing material.

As one example, we may characterize capacitance vs. relative humidity (RH) at various temperatures (and optionally pressures). This characterization can be in the form of numbers or a mathematic formula such as a polynomial. We perform a similar characterization of resonant frequency vs. RH, also at various temperatures (and optionally pressures). Next, we combine these two datasets, and eliminate the variable RH, so that we have a database of calibration values with Capacitance vs. Resonant Frequency at various temperatures (and optionally pressures). For analytes such as methane and carbon dioxide, the target gases do not affect the capacitance, or their effect on the capacitance is negligible. Water has a strong effect on capacitance. The database of capacitance vs. resonant frequency is our water calibration database (e.g., a lookup table or mathematic formulas in the memory of the processor 48).

One example of a suitable algorithm is as follows: at each point in time, we measure the capacitance, convert the capacitance measurement to frequency using our calibration table, then subtract that frequency from the actual measured resonant frequency of the resonator. The result is a frequency change that corresponds only to the analyte of interest adsorbed in the sensing material. Optionally, we can take the capacitance measurement and convert it to RH using the calibration data table just described above. This way, the device reports both RH and analyte concentration, which may be displayed to an end-user via display 52, or otherwise communicated or recorded.

There are many other ways in which measurements of both capacitance and mechanical or electromechanical response of the oscillator may be used to calculate the analyte value and optionally a humidity value (typically by algorithms, calibration curves or calibration data, and/or look-up tables). Generally, the response of the oscillator (e.g., frequency response) indicates a combined mass of substances (water and analyte) adsorbed in the sensing material 30, and the capacitance measurement indicates the contribution of water to be subtracted (or accounted for) from the total combined mass of substances adsorbed or absorbed in the sensing material. Thus, the device is able to distinguish between water and analyte in the mass loading, and reports the analyte value accurately independent of humidity.

Figure 9:
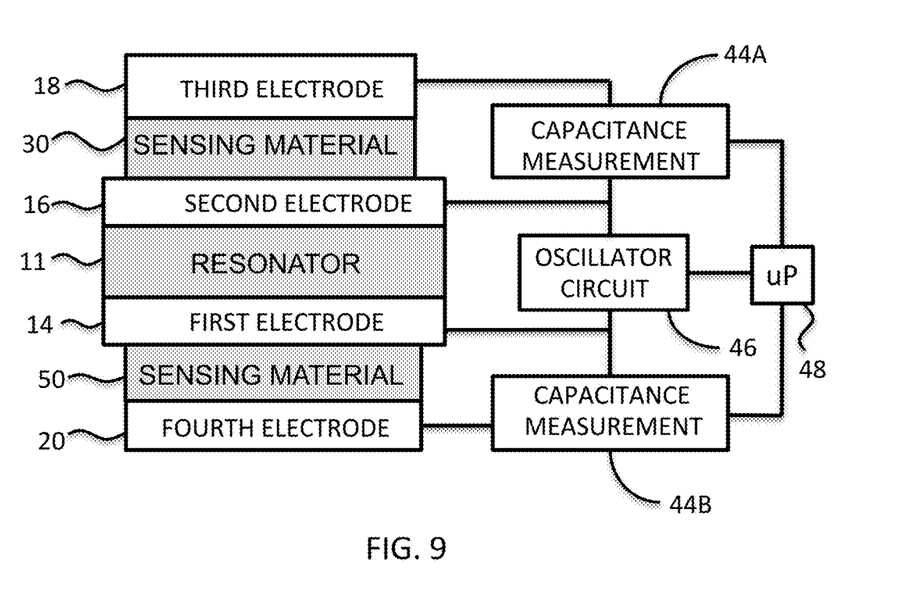
FIG. 9 is a schematic, side view of a sensor device having capacitors with sensing materials disposed on both sides of a resonator according to another embodiment of the invention.

FIG. 9 shows another embodiment of a sensor device that is similar to the device of FIG. 6 previously described above. However, the device of FIG. 9 has two capacitors with sensing material positioned on opposite sides of the resonator 11. In particular, the device of FIG. 9 further includes additional sensing material 50 disposed on the first electrode 14. Thus, sensing materials 30 and 50 are positioned on opposite sides of the resonator 11. The sensing materials 30 and 50 are preferably MOF films that are grown or deposited directly on the second (front) 16 electrode and first (back) electrode 14, respectively. The sensing materials 30 and 50 are preferably the same material for adsorbing the same target analyte. In alternative embodiments, the sensing materials 30 and 50 can be two different types of sensing films that can sense two different target analytes (e.g., methane and carbon dioxide). A first capacitor is formed by the second and third electrodes 16 and 18 with a layer of the first sensing material 30 positioned (e.g., sandwiched) between the second and third electrodes. In addition, a second capacitor is formed by the first electrode 14 and a fourth electrode 20 that is disposed on the additional sensing material 50 such that the layer of sensing material 50 is positioned (e.g., sandwiched) between the first and fourth electrodes 14 and 20. The first and fourth electrodes 14 and 20 are preferably parallel plates or layers of metal, with the fourth electrode 20 being gas-permeable.

As in previous embodiments, the readout circuit preferably includes the oscillator circuit 46 connected to the first electrode 14 and to the second electrode 16 to drive the oscillating motion of the resonator 11 and to measure a mechanical or electromechanical response of the oscillating portion. A first capacitance measurement circuit 44A is connected to the second electrode 16 (shared electrode) and to the third electrode 18 to measure a capacitance of the first capacitor formed by the second and third electrodes 16 and 18 when the substances are adsorbed or absorbed in the sensing material 30. The measurement of capacitance can be accomplished via a high-precision capacitance measurement method, such as a relaxation oscillator or a $\Sigma$-$\Delta$ capacitance-to-digital converter.

In some embodiments, a second capacitance measurement circuit 44B is connected to the first electrode 14 (another shared electrode) and to the fourth electrode 20 to measure a capacitance of the second capacitor formed by the first and fourth electrodes 14 and 20 when the substances are adsorbed or absorbed in the sensing material 50. The processor 48 is in communication (wirelessly or with wires) with the oscillator circuit 46 and the capacitance measurement circuits 44A and 44B to receive signals or data indicative of the electromechanical response and the first and second capacitance measurements. Although the first and second capacitance measurement circuits 44A and 44B are drawn separately for clarity of understanding in the patent drawings, it is not necessary to have two separate capacitance measurement circuits to measure individual capacitances of the first and second capacitors. In other embodiments, there is a single capacitance measurement circuit to measure a total capacitance of both the first and second capacitors. In addition, the capacitance measurement circuit and the oscillator circuit 46 are typically part of the same overall electronic readout circuit under the control of the microprocessor 48.

The double-sided sensor device having first and second capacitors positioned on opposite sides of the resonator 11 has several advantages. The symmetry of the two capacitors on opposite sides of the resonator 11 ensures symmetric (stress free) operation of the resonator with reduced likelihood that the resonator experiences out of plane warping during operation. The fourth electrode 20 is preferably gas-permeable (e.g. porous, slotted, interdigitated, or serpentine) so that the sensing material 50 is accessible to analyte molecules in a sample or in the environment to which the sensor is exposed. The double-sided placement of the sensing materials 30 and 50 on opposite sides of the resonator 11 may increase the sensitivity of the sensor device for detecting analyte. In addition, the two capacitors provide an increase in the total capacitance which is easier to measure, in those embodiments in which the capacitance measurement circuit measures the total capacitance of the first and second capacitors.

Figure 10:
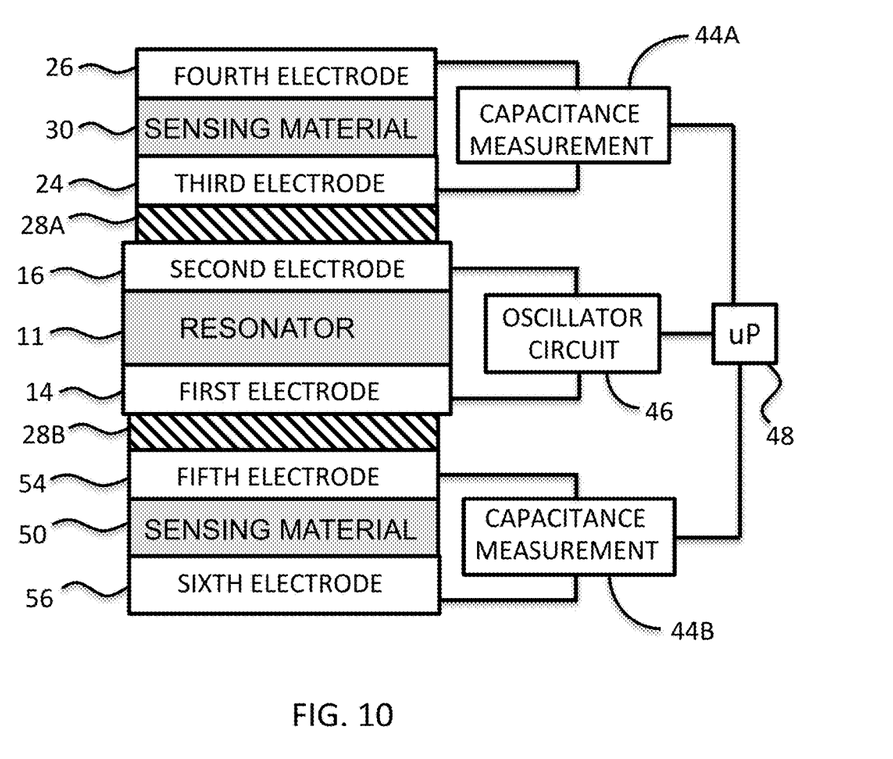
FIG. 10 is a schematic, side view of another sensor device having capacitors with sensing materials disposed on both sides of a resonator according to another embodiment of the invention.

FIG. 10 shows another example of a double-sided sensor device having first and second capacitors disposed on opposite sides of the resonator 11. In this example, the device includes six electrodes rather than four electrodes (with 2 shared electrodes) previously described with reference to FIG. 9. As in the previous example, the device of FIG. 10 includes the resonator 11 and first and second electrodes 14, 16 coupled to opposite sides of the resonator 11. The first and second electrodes 14 and 16 are positioned to apply a potential difference across the resonator to drive an oscillating motion of the resonator 11. The first capacitor is formed by third and fourth electrodes 24 and 26 with the sensing material 30 positioned between the third and fourth electrodes 24 and 26. The first capacitor is positioned on the oscillating portion of the resonator 11 by means of a first insulating layer 28A that separates the third electrode 24 from the second electrode 16. The fourth electrode 26 should be gas-permeable (e.g. porous, slotted, interdigitated, or serpentine) to ensure that the sensing material 30 is accessible to molecules in a sample or environment to which the sensor is exposed.

The second capacitor is formed by fifth and sixth electrodes 54 and 56 with the additional sensing material 50 sandwiched between the fifth and sixth electrodes 54 and 56. The second capacitor is positioned on the oscillating portion of the resonator 11 by means of a second insulating layer 28B that separates the fifth electrode 54 from the first electrode 14. The second capacitor is positioned on the opposite side of the resonator 11 relative to the first capacitor formed by the third and fourth electrodes 24 and 26. The fifth and sixth electrodes 54 and 56 are preferably parallel plates or layers of metal. The sixth electrode 56 is gas-permeable so that the sensing material 50 is accessible to target analyte. In some embodiments, the sensing materials 30 and 50 are the same material for adsorbing the same target analyte. The double-sided placement of the sensing materials 30 and 50 on opposite sides of the resonator 11 may increase sensitivity of the sensor device. In other embodiments, the sensing materials 30 and 50 can be two different types of sensing films that can sense two different target analytes.

In alternative embodiments, the sixth electrode 56 is not gas-permeable so that the sensing material 50 is not accessible to molecules in a sample or environment to which the sensor is exposed. Or the second capacitor is covered or sealed so that substances do not adsorb in the additional sensing material 50. In these alternative embodiments, the second capacitor functions as a reference sensor. The covered or sealed capacitor on the opposite side from the gas-permeable capacitor can serve as a reference for every change in operating conditions which is not due to gas absorption (e.g., temperature, stress, drift, etc.). There is also the advantage that the symmetry of the two capacitors on opposite sides of the resonator ensures symmetric (stress free) operation of the resonator with reduced likelihood that the resonator experiences out of plane warping during operation.

The resonator device according to embodiments of the present invention is a suitable gas sensor for many consumer applications. The resonator device remains simple and low cost by adding only one more metallization layer and solves the humidity problem by augmenting the capabilities of the electronic readout circuit to include a capacitance measurement. The device may be miniature in some embodiments. For example, the device comprising the resonant sensor with capacitor and oscillator circuit (without a processor) preferably has a cubic structure of dimensions less than or equal to: 5×5×1 mm. A processor may be included or separate.

The processor 48 may be a microprocessor included with the device (e.g., a small 8 bit low-cost processor). Alternatively, processing functions may be performed in a separate processor or external computer in communication with the one or more readout circuits. The external processor or computer receives data representative of the measured capacitance and response of the oscillator (e.g. frequency shifts or resonance frequencies) and determines the analyte value and optionally humidity value. Alternatively, multiple processors may be provided, e.g., providing one or more processors in the device that communicate (wirelessly or with wires) with one or more external processors or computers.

Some processing of data can be done near the resonant sensor. For instance, time averaging or multiplexing or digitization can be all processed in the vicinity of the sensor before being transmitted to a computer or a circuit board with a multiprocessor. Specific algorithms can be loaded in memory to perform the same functions one would in a digital computer and then drive displays where colored outputs can be used to indicate level of detection or hazard. As in many sensors deployed today, such as RF tags and implanted medical devices, it is possible to use RF antennas to couple and provide power to the sensor. Once a sensor is powered, it senses its function, and then the output of the sensor is re-radiated to a receiving antenna. In this fashion, the device can be passive and remotely addressed.

The above description illustrates embodiments of the invention by way of example and not necessarily by way of limitation. Many other embodiments are possible. For example, only one sensor element was shown at a time for simplicity of understanding in the patent drawings, but arrays of sensors are also possible in alternative embodiments. Arrays of resonant sensors may be functionalized with MOFs or polymer films having different properties so that the sensor array can sensitively detect and differentiate multiple target analytes, chemical compounds, and even complex mixtures. In addition, the device may include different types of sensors, such as a pressure sensor and/or a temperature sensor for detecting pressure and temperature and using these data in the calculations. Further, the sensor device may include a temperature feedback control loop with a heater and temperature sensor.

Accordingly, the scope of the invention should be determined by the following claims and their legal equivalents.

What is claimed is:

1. A device for detecting at least one analyte, the device comprising:
   a) at least one resonant sensor having an oscillating portion;
   b) at least a first capacitor positioned on a first side of the oscillating portion, wherein the first capacitor is formed by at least two electrodes and a sensing material positioned between the electrodes;
   c) at least one readout circuit arranged to measure a response of the oscillating portion when the analyte and water are adsorbed or absorbed in the sensing material; and
   d) at least one capacitance measurement circuit arranged to measure a capacitance between the electrodes, whereby the capacitance measurement indicates an amount of the water in the sensing material to permit correction of an analyte value for the effects of humidity.

2. The device of claim 1, wherein the electrodes comprise substantially parallel layers or plates of metal, and at least one of the electrodes is gas-permeable to permit molecules to pass through to the sensing material.

3. The device of claim 1, further comprising a second capacitor positioned on an opposite side of the oscillating portion from the first capacitor, wherein the second capacitor is formed by at least two more electrodes with additional sensing material positioned therebetween.

4. The device of claim 3, wherein at least one of the electrodes forming the second capacitor is gas-permeable, and the capacitance measurement circuit is connected to the four electrodes forming the first and second capacitors to measure a total capacitance of the capacitors.

5. The device of claim 1, wherein the resonant sensor comprises a quartz crystal having a circular surface, and the capacitor is positioned substantially at the center of the circular surface.

6. The device of claim 1, further comprising at least one processor in communication with the readout circuit and the capacitance measurement circuit for receiving signals or data indicative of the capacitance measurement and the response of the oscillating portion, wherein the processor is programmed to determine the analyte value in dependence upon the measurements of both the capacitance and the response of the oscillating portion.

7. The device of claim 6, wherein the response of the oscillating portion is indicative of the combined mass of the water plus the analyte adsorbed or absorbed in the sensing material, and the processor is programmed to determine the analyte value by using the capacitance measurement to determine a contribution of the water to the response of the oscillating portion or to the combined mass indicated by the response.

8. The device of claim 6, wherein the processor is further programmed to calculate at least one humidity value from the capacitance measurement.

9. The device of claim 1, wherein the resonant sensor includes a mechanical resonator and first and second electrodes coupled to opposite sides of the mechanical resonator, the sensing material is disposed on the second electrode, the capacitor is formed by the second electrode and a third electrode disposed on the sensing material such that the sensing material is positioned between the second and third electrodes, and the third electrode is gas-permeable.

10. The device of claim 9, further comprising a second capacitor formed by the first electrode and a fourth electrode with additional sensing material positioned between the first and fourth electrodes, wherein the capacitance measurement circuit is connected to the four electrodes forming the first and second capacitors to measure a total capacitance of the first and second capacitors or individual capacitances of the first and second capacitors.

11. The device of claim 1, wherein the device has a length that is less than or equal to 5 mm, a width less than or equal to 5 mm, and a height less than or equal to 1 mm.

12. The device of claim 1, wherein the sensing material comprises a porous crystalline material that adsorbs or absorbs target molecules of the analyte having a relative permittivity lower than the relative permittivity of water.

13. A sensor device for detecting at least one analyte, the device comprising:
 a) at least one resonator having an oscillating portion;
 b) first and second electrodes positioned to apply a potential difference across the resonator to drive an oscillating motion of the oscillating portion;
 c) a sensing material disposed on the second electrode;
 d) a third electrode disposed on the sensing material such that the sensing material is positioned between the second and third electrodes, wherein the third electrode is gas-permeable;
 e) at least one readout circuit arranged to measure a response of the oscillating portion when the analyte and water are adsorbed or absorbed in the sensing material; and
 f) at least one capacitance measurement circuit arranged to measure a capacitance between the second and third electrodes, whereby the capacitance measurement indicates an amount of the water in the sensing material to permit correction of an analyte value for the effects of humidity.

14. The device of claim 13, wherein the second and third electrodes comprise substantially parallel layers or plates of metal.

15. The device of claim 13, further comprising at least one processor in communication with the readout circuit and the capacitance measurement circuit for receiving signals or data indicative of the response of the oscillating portion and the capacitance, wherein the processor is programmed to determine the analyte value in dependence upon the measurements of both the response of the oscillating portion and the capacitance.

16. The device of claim 13, wherein the sensing material comprises a porous crystalline material that adsorbs or absorbs target molecules of the analyte having a relative permittivity lower than the relative permittivity of water.

17. A method for detecting at least one analyte with correction for effects of water, the method comprising:
 a) exposing at least one resonant sensor to a sample or to an environment, wherein the resonant sensor includes at least one oscillating portion, at least one a first capacitor is positioned on a first side of on the oscillating portion, and the capacitor is formed by at least two electrodes and a sensing material positioned between the electrodes;
 b) measuring a response of the oscillating portion when the analyte and water are adsorbed or absorbed in the sensing material;
 c) measuring a capacitance between the electrodes, wherein the capacitance measurement indicates an amount of the water in the sensing material; and
 d) utilizing at least one processor to determine at least one analyte value according to both measurements of the response of the oscillating portion and the capacitance.

18. The method of claim 17, wherein the electrodes comprise substantially parallel layers or plates of metal, and at least one of the electrodes is gas-permeable.

19. The method of claim 17, wherein the response of the oscillating portion is indicative of the combined mass of the water plus the analyte adsorbed or absorbed in the sensing material, and the analyte value is determined by using the capacitance measurement to determine a contribution of the water to the response of the oscillating portion or to the combined mass indicated by the response.

20. The method of claim 17, wherein the sensing material comprises a porous crystalline material that adsorbs or absorbs target molecules of the analyte having a relative permittivity lower than the relative permittivity of the water.

* * * * *